(12) United States Patent
Malkar et al.

(10) Patent No.: US 10,709,323 B2
(45) Date of Patent: Jul. 14, 2020

(54) PREPARATION OF SUBJECTS FOR MEDICAL OR VETERINARY EXAMINATION

(71) Applicant: OWLSTONE MEDICAL LIMITED, Cambridge (GB)

(72) Inventors: Aditya Malkar, Cambridge (GB); Lauren Brown, Cambridge (GB); Marc Van Der Schee, Cambridge (GB)

(73) Assignee: Owlstone Medical Limited (GB)

( * ) Notice: Subject to any disclaimer, the term of this patent is extended or adjusted under 35 U.S.C. 154(b) by 0 days.

(21) Appl. No.: 16/482,382

(22) PCT Filed: Feb. 5, 2018

(86) PCT No.: PCT/GB2018/050321
§ 371 (c)(1),
(2) Date: Jul. 31, 2019

(87) PCT Pub. No.: WO2018/142162
PCT Pub. Date: Aug. 9, 2018

(65) Prior Publication Data
US 2019/0357763 A1 Nov. 28, 2019

(30) Foreign Application Priority Data
Feb. 6, 2017 (GB) .................................. 1701913.4

(51) Int. Cl.
*G01N 27/62* (2006.01)
*A61B 1/31* (2006.01)
(Continued)

(52) U.S. Cl.
CPC .............. *A61B 1/31* (2013.01); *G01N 27/624* (2013.01); *G01N 33/487* (2013.01); *G01N 33/4833* (2013.01); *G01N 33/50* (2013.01)

(58) Field of Classification Search
CPC .... A61B 1/31; G01N 27/624; G01N 33/4833; G01N 33/487; G01N 33/50
See application file for complete search history.

(56) References Cited

U.S. PATENT DOCUMENTS 10,226,238 B2 * 3/2019 Pannell .................... A61B 1/31
2008/0054174 A1   3/2008 Boyle et al.
(Continued)

FOREIGN PATENT DOCUMENTS

WO   WO 2010/141751   12/2010
WO   WO 2016/038377   3/2016

OTHER PUBLICATIONS

Taylor, E. W., et al. "Bowel preparation and the safety of colonoscopic polypectomy." Gastroenterology 81.1 (1981): 1-4. (Year: 1981).*
(Continued)

*Primary Examiner* — Wyatt A Stoffa
(74) *Attorney, Agent, or Firm* — Barnes & Thornburg LLP

(57) ABSTRACT

Disclosed is a method of identifying if a subject is sufficiently prepared to permit successful colonoscopic examination, the method comprising the steps of: (a) obtaining a stool sample from a subject having undergone preparation for a colonoscopic examination; (b) analysing the sample to detect the presence and/or amount of faecal matter, if any, in the stool sample; and (c) from the analysis in step (b), identifying whether the subject has been sufficiently prepared.

4 Claims, 1 Drawing Sheet

Adequately prepped

Figure 1B:
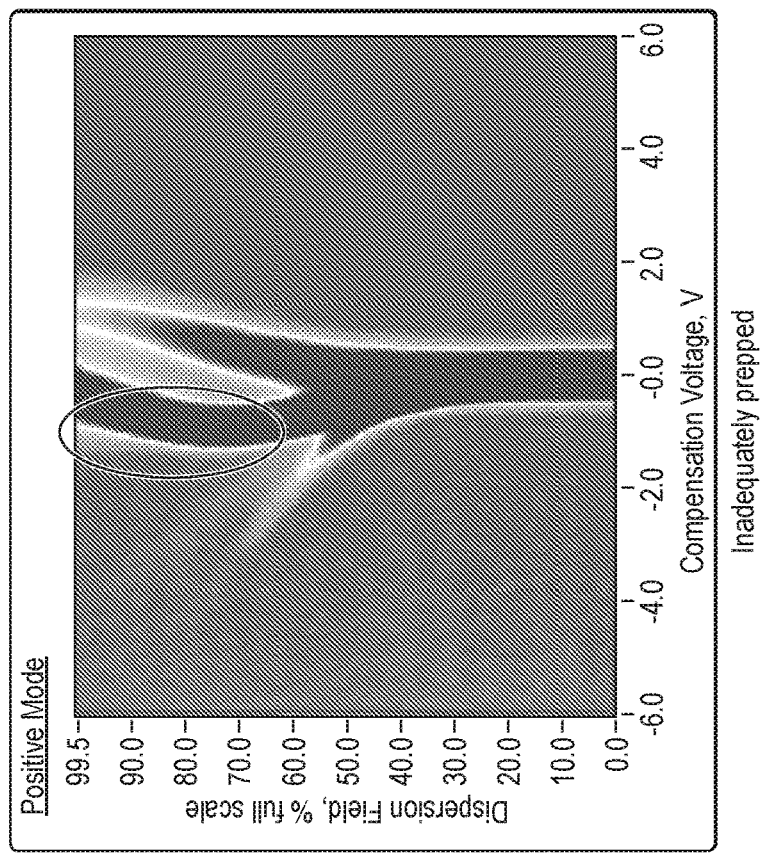

(51) Int. Cl.
*G01N 33/483* (2006.01)
*G01N 33/487* (2006.01)
*G01N 33/50* (2006.01)

(56) References Cited

U.S. PATENT DOCUMENTS

| | | | |
|---|---|---|---|
| 2009/0305331 A1* | 12/2009 | Ben-Horin | G01N 33/50 435/29 |
| 2011/0053867 A1 | 3/2011 | Caswell | |
| 2011/0053868 A1 | 3/2011 | Delaney et al. | |
| 2014/0100176 A1 | 4/2014 | Delaney et al. | |

OTHER PUBLICATIONS

Clark et al., "Quantification of Adequate Bowel Preparation for Screening or Surveillance Colonoscopy in Men," Gastroenterology, 150:396-405 (2016).
Zakko et al., Detection of Inadequate Bowel Preparations Prior to Colonoscopy via field Asymmetric Ion Mobility Spectrometer Analysis of Volatile Organic Compounds from Colonic Effluent Samples, Gastroenterology, 152(5): S426 (2017), Apr. 2017.
Int'l Preliminary Report on Patentability issued in App. No. PCT/GB2018/050321 (dated 2019).
Search Report & Written Opinion issued in App. No. PCT/GB2018/050321 (dated 2018).

* cited by examiner

PREPARATION OF SUBJECTS FOR MEDICAL OR VETERINARY EXAMINATION

CROSS REFERENCE TO RELATED APPLICATIONS

This application is a U.S. nationalization under 35 U.S.C. § 371 of International Application No. PCT/GB2018/050321, filed Feb. 5, 2018, which claims priority to United Kingdom Patent Application No. 1701913.4, filed Feb. 6, 2017. The disclosures set forth in the referenced applications are incorporated herein by reference in their entireties.

FIELD OF THE INVENTION

The present invention concerns a method for checking whether a subject, especially a human subject, is adequately prepared to undergo a medical examination procedure.

BACKGROUND OF THE INVENTION

A common medical examination is colonoscopy, in which a colonoscope is inserted into the colon. Typically the procedure is performed to visually check for the presence of polyps or other pre-cancerous or cancerous growths in the colon. Any polyps detected may be simultaneously removed.

To improve the likelihood of any polyps present in the colon being detected, it is necessary that the colon is substantially clear of faecal matter, to facilitate visual inspection of the colon. In order to achieve this, subjects who are to undergo colonoscopy must be prepared. Such preparation involves ingestion of a laxative to purge the colon. Typical laxative preparations for this purpose are sold under various product names such as Klean-Prep® and Moviprep.

Occasionally however subjects are inadequately prepared for colonoscopy, and too much faecal matter remains in the colon to permit reliable detection of small polyps which might nevertheless develop into cancers. In such circumstances, the colonoscopic investigation has to be halted and another appointment made. This is wasteful of medical resources and extremely inconvenient for the subject. At present no effective method has been described to detect such poor subject preparation prior to actual colonoscope insertion into the subject.

SUMMARY OF THE INVENTION

In a first aspect, the present invention provides a method of identifying if a subject is sufficiently prepared to permit colonoscopic examination, the method comprising the steps of:
 (a) obtaining a stool sample from a subject having undergone preparation for a colonoscopic examination;
 (b) analysing the sample to detect the presence and/or amount of faecal matter, if any, in the stool sample; and
 (c) from the analysis in step (b), identifying whether the subject has been sufficiently prepared.

The colonoscopic examination may be a veterinary procedure but more normally the subject is a human. The subject will have been prepared for the colonoscopic examination by a process that will usually comprise the administration of a laxative. The stool sample collected from the subject will normally therefore be highly liquid.

The inventors have found that simple visual inspection of liquid stool samples is not a reliable indication of whether the subject is sufficiently prepared to permit successful colonoscopic examination. For example, a stool sample could be largely free of particulates, but there may be faecal matter adhering to the colon which would interfere with a colonoscopic investigation. Accordingly a more sensitive technique than simple visual examination is required. For present purposes, a subject is considered sufficiently prepared if the colon is clear enough to permit the visual detection of polyps down to a size of 5 mm.

Preferred analytic techniques for performing the analysis of step (b) are those which detect the presence of faecal matter in the stool sample by detection of volatile organic compounds ("VOC") which are characteristic of such faecal matter. A particularly preferred technique comprises FAIMS (Field Asymmetric Ion Mobility Spectrometer) analysis. FAIMS analysis of samples can be performed within about 15 minutes, and so a stool sample taken from a subject at the start of their clinical or hospital appointment can be analysed and the results obtained without lengthy delay, permitting the clinician to defer further processing of the subject (e.g. by administration of a sedative) until the FAIMS analysis has been completed and the clinician can be confident that the subject's colon is sufficiently clear.

Other analytical techniques could be used, such as GC-MS, but these typically require greater sample processing or otherwise take longer to perform and require large and expensive apparatus.

Commercial FAIMS analysis apparatus is available under the trade name LONESTAR® from Owlstone Nanotech Inc.

The person skilled in the art is familiar with the principles of FAIMS analysis which are explained in, for example, U.S. Pat. No. 7,498,570 and Covington et al., (Analyst 2015; 140, 6775-6781 "The application of FAIMS gas analysis in medical diagnostics").

In outline, vapour from a sample is ionized and passed between two parallel conducting plates. An alternating voltage applied across the plates creates an alternating electric field between them (known as the "dispersion field", DF). The voltage has a short-duration, high-amplitude positive profile, followed by a long-duration, low-amplitude negative profile. The product of the voltage and pulse duration is equal (but opposite) for the positive and negative portions of the profile, such that an ion in the field will move up and down by the same amount during the positive and negative voltage profiles (i.e. the net vertical movement will be zero), allowing the ion to pass through the channel between the plates. However, this holds true only if the mobility of the ion is the same under both the high- and low-strength field conditions. Normally, the mobility of the ion varies with field strength.

In order to control which ions pass through the channel, an additional DC voltage (the "compensation voltage", CV) is applied between the plates.

The value of the CV can be adjusted to compensate for the net vertical drift of a particular ion. By scanning through various values of CV, and recording the magnitude of the ion current emerging from the channel at the various CV values, it is possible to detect the various types of ion present in the sample.

By additionally operating at different values of DF, as well as CV, it is possible to build up a FAIMS spectrum of current intensity at different combinations of DF and CV, which permits a very high level of discrimination between different samples.

Accordingly, in a preferred embodiment of the method of the invention, steps (b) and (c) comprise measuring the ion current intensity at one or more pairs of values for dispersion field and compensation voltage, and comparing the measured ion current intensity to a respective predetermined threshold value at each of the one or more pairs of values for dispersion field and compensation voltage, and from the comparison, determining whether or not the subject is sufficiently prepared for colonoscopic examination.

As an example, it is possible to build up a database of pairs of values for dispersion field and compensation voltage and associated ion current intensity at those values, for subjects who were subsequently found to have been sufficiently prepared for colonoscopic examination. Equally, of course, the data from the subject could instead (or additionally) be compared with data compiled from subjects who were subsequently found to have been insufficiently prepared for colonoscopic examination. The database or databases can, for instance, take the form of a "heat map", but any other suitable means of storing or representing the data could be used. In this instance, one can compare the data from the subject with the data in the compiled database or databases. The advantage of a 'heat map' approach is that it allows a convenient visual comparison to be made between the data from the subject and a composite heat map representing data obtained from a plurality of sufficiently well-prepared subjects and/or a composite heat map representing data obtained from a plurality of insufficiently prepared subjects. In this way, one can compare a heat map from the subject, or specific portions or regions thereof, with the composite heat map (or the corresponding specific portions or regions thereof) from well-prepared and/or insufficiently prepared subjects. Alternatively of course the data can be compared in a non-visual e.g. numerical manner by a computer, for example by comparing data obtained from the subject with numerical threshold values obtained by analysis of a plurality of sufficiently prepared and/or insufficiently prepared subjects. In a preferred embodiment data (e.g. ion current density data) from the subject for one or more pairs of values of dispersion field and compensation voltage are compared to threshold values at each of the one or more pairs of values dispersion field and compensation voltage, the threshold values having been derived previously by analysis of data from a plurality of sufficiently prepared and/or insufficiently prepared subjects. Subject data values above or below the threshold values (as appropriate) will indicate whether or not the subject is sufficiently well prepared for colonoscopic examination.

With the benefit of the analysis, a clinician can predict whether a subject is unlikely to be sufficiently well prepared for a successful colonoscopic examination and, if appropriate, end the appointment early before proceeding as far as colonoscopic insertion. This reduces wastage of hospital resources and reduces subject inconvenience. In the alternative, if the analysis suggests that the subject is likely to be sufficiently well prepared, the clinician can proceed with sedation of the subject and continue with good expectation of a successful examination.

Figure 1A:
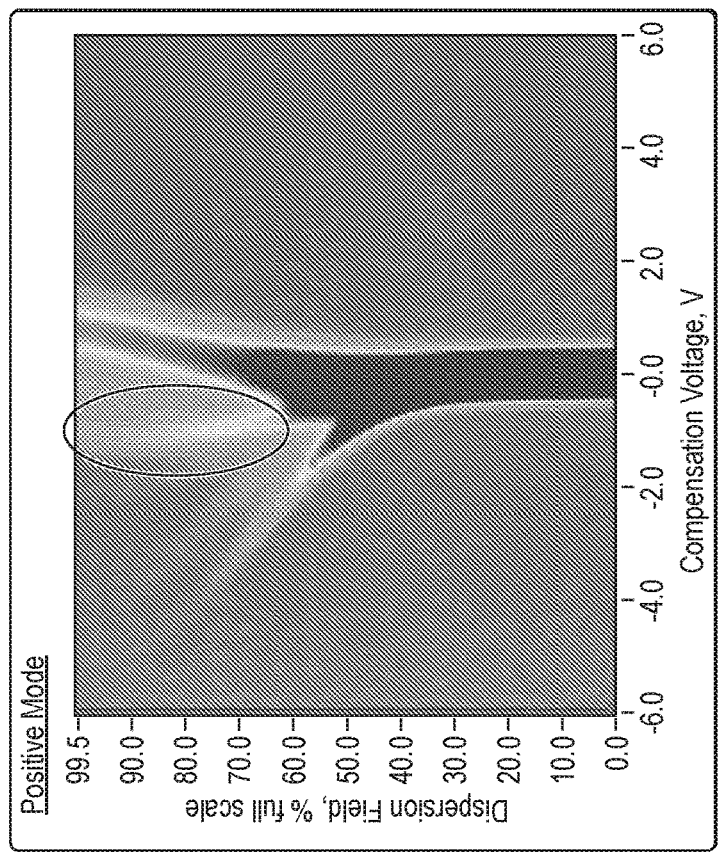

The invention will now be further described by way of illustrative example, and with reference to the accompanying drawings, FIGS. 1A and 1B, which are illustrations of typical FAIMS spectra for stool samples from a subject who has (1A) or who has not (1B) been sufficiently prepared for colonoscopic examination.

EXAMPLE

To obtain stool samples for analysis, patients were asked to provide rectal effluent samples before colonoscopy evaluation. Collected samples were frozen and stored at −80° C. until ready for analysis. Adequate bowel preparation (defined as ability to detect all polyps ≥5 mm) was determined by the endoscopist's assessment during the subsequent colonoscopy.

Prior to analysis, samples were thawed in a fridge overnight and a 5 mL aliquot was taken from each sample for analysis via FAIMS using the Lonestar® Gas Analyzer (Owlstone Medical Ltd.). Aliquots were heated to 50° C. and head space gases were run through the FAIMS system to create spectra for VOC.

A full scan of DF and CV values were obtained for each sample.

A commercially available software package (SIMCA from MKS Data Analytics Solutions) was used to analyse the data and identify pairs of values for DF and CV where the resulting ion current was significantly altered between samples from adequately prepared and inadequately prepared individuals.

FIG. 1A illustrates a typical FAIMS spectrum for a stool sample from a subject found to have been adequately prepared, whilst FIG. 1B is a typical spectrum for a stool sample from a subject found to have been inadequately prepared.

Each spectrum takes the form of a heatmap of the ion current intensity (arbitrary units) at different relative dispersion field strength, DF, (as a percentage of the maximum DF value), and compensation voltage (CV) values from −6.0 to +6.0V. The ion current intensity is shown as a colour in the originally-produced heatmaps, and here reproduced on a grey scale.

It is apparent from a superficial visual comparison of the two spectra that there are several points of distinction between the heatmaps, and this was confirmed by multivariate analysis using the SIMCA package mentioned above. The circled portions of FIGS. 1A and 1B indicate regions of the heatmaps which are significantly different between samples from adequately prepared subjects and those from inadequately prepared subjects.

From these experiments it is straightforward to identify one or more particular pairs of DF and CV values which can be used to characterise a sample as being from an adequately prepared subject or an inadequately prepared subject, depending on the ion current intensity. Typically, statistical analysis will be performed to establish a threshold value for each of the said one or more pairs of DF and CV co-ordinates, and an ion current intensity above or below the relevant threshold will be indicative of the subject being adequately or inadequately prepared, as the case may be. It may be that a single pair of DF/CV co-ordinates will be sufficient to provide good discrimination, but it is expected that the quality of the test will be improved by analysis of a plurality of DF/CV co-ordinates, preferably at well-separated portions of the FAIMS spectra. This can be done using the onboard software provided with commercially available FAIMS analysis equipment (e.g. Owlstone Limited's Lonestar portable FAIMS analysis equipment).

CONCLUSION

Subjects with inadequate bowel preparation can be identified from rectal effluent samples using FAIMS. The high sensitivity and specificity are encouraging. This technique provides an effective pre-endoscopic test to ensure patients have adequate bowel preparation for effective colonoscopy.

The invention claimed is:

1. A method of identifying if a subject is sufficiently prepared to permit successful colonoscopic examination, the method comprising the steps of:
   (a) obtaining a stool sample from a subject having undergone preparation for a colonoscopic examination;
   (b) analysing the sample using an analytic technique comprising Field Asymmetric Ion Mobility Spectrometer analysis which detects volatile organic compounds collected or derived from the stool sample to detect the presence and/or amount of faecal matter, if any, in the stool sample; and
   (c) from the analysis in step (b), identifying whether the subject has been sufficiently prepared.

2. The method according to claim 1, wherein prior to obtaining a stool sample from the subject, the subject has been administered a laxative.

3. The method according to claim 1 or 2, wherein the subject is a human subject.

4. The method according to claim 1, wherein steps (b) and (c) comprise measuring the ion current intensity at one or more pairs of values for dispersion field and compensation voltage, and comparing the measured ion current intensity to a respective predetermined threshold value at each of the one or more pairs of values for dispersion field and compensation voltage, and from the comparison, determining whether or not the subject is sufficiently prepared for colonoscopic examination.

* * * * *